(12) United States Patent
Cahill

(10) Patent No.: US 9,557,308 B2
(45) Date of Patent: Jan. 31, 2017

(54) RAPID RESPONSE VOLCANIC ASH DETECTOR

(71) Applicant: University of Alaska Fairbanks, Fairbanks, AK (US)

(72) Inventor: Catherine Cahill, Fairbanks, AK (US)

(73) Assignee: UNIVERSITY OF ALASKA FAIRBANKS, Fairbanks, AA (US)

( * ) Notice: Subject to any disclaimer, the term of this patent is extended or adjusted under 35 U.S.C. 154(b) by 588 days.

(21) Appl. No.: 13/972,378

(22) Filed: Aug. 21, 2013

(65) Prior Publication Data

US 2014/0053629 A1    Feb. 27, 2014

Related U.S. Application Data

(60) Provisional application No. 61/691,753, filed on Aug. 21, 2012.

(51) Int. Cl.
| | | |
|---|---|---|
| *G01N 33/00* | (2006.01) | |
| *G01N 15/02* | (2006.01) | |
| *G01N 15/06* | (2006.01) | |
| *G01N 1/22* | (2006.01) | |

(52) U.S. Cl.
CPC .......... *G01N 33/0063* (2013.01); *G01N 15/02* (2013.01); *G01N 15/06* (2013.01); *G01N 2001/2279* (2013.01)

(58) Field of Classification Search
CPC .................................................. G01N 33/0063
USPC ....... 73/31.01, 31.02, 170.16, 170.28, 28.01; 340/601, 963
See application file for complete search history.

(56) References Cited

U.S. PATENT DOCUMENTS

| | | | | |
|---|---|---|---|---|
| 5,074,137 A | * | 12/1991 | Harris | A23L 3/3418 73/31.02 |
| 7,000,454 B2 | * | 2/2006 | Schneider | B08B 3/08 73/31.03 |
| 7,812,306 B2 | * | 10/2010 | Fissan | G01N 23/00 250/281 |
| 8,461,531 B2 | * | 6/2013 | Tillotson | G01N 21/71 250/338.1 |
| 8,706,320 B2 | * | 4/2014 | Kelm | G01N 1/2202 340/601 |
| 2006/0187070 A1 | * | 8/2006 | Liang | B01D 46/008 340/607 |
| 2012/0068862 A1 | * | 3/2012 | Tillotson | B64D 45/00 340/963 |

* cited by examiner

*Primary Examiner* — Michael A Lyons
*Assistant Examiner* — Hoang Nguyen
(74) *Attorney, Agent, or Firm* — Ballard Spahr LLP

(57) ABSTRACT

Methods and systems for detecting ambient aerosols are disclosed. An example method can comprise receiving an air sample comprising aerosol particles. A method can comprise determining at least one of concentration of the aerosol particles and size of an aerosol particle from the aerosol particles. A method can also comprise determining a composition of the air sample if at least one of the concentration exceeds a first predetermined threshold and the size exceeds a second predetermined threshold. A method can further comprise providing a notification indicating the presence of volcanic ash based on the determined composition of the aerosol.

20 Claims, 6 Drawing Sheets

RAPID RESPONSE VOLCANIC ASH DETECTOR

CROSS REFERENCE TO RELATED PATENT APPLICATION

This application claims priority to U.S. Provisional Application No. 61/691,753 filed Aug. 21, 2012, herein incorporated by reference in its entirety.

SUMMARY

It is to be understood that both the following general description and the following detailed description are exemplary and explanatory only and are not restrictive, as claimed. Provided are methods and systems for detecting ambient aerosols. An example method can comprise receiving an air sample comprising aerosol particles. At least one of concentration of the aerosol particles and size of an aerosol particle from the aerosol particles can be determined. A composition of the air sample can be determined if at least one of the concentration exceeds a first predetermined threshold and the size exceeds a second predetermined threshold. A notification indicating the presence of volcanic ash can be provided based on the determined composition of the aerosol.

In another aspect, an example method can comprise measuring concentration and size of ambient aerosols in an air stream. A first notification can be provided if at least one of the size of the ambient aerosols exceeds a first threshold and the concentration of the ambient aerosols exceeds a second threshold. Composition information of the ambient aerosols can be determined. A second notification can be provided if the composition information indicates presence of volcanic ash in the air stream.

In another aspect, an example system can comprise a first sensor for measuring at least one of concentration of ambient aerosols and size of ambient aerosols. The system can also comprise a second sensor for determining composition information of the ambient aerosols. The system can further comprise a device configured to generate a first notification if at least one of the concentration of the ambient aerosols exceeds a first threshold and the size of the ambient aerosols exceeds a second threshold. The device can further be configured to generate a second notification if the composition information matches signature data indicative of volcanic ash within a specified confidence level.

Additional advantages will be set forth in part in the description which follows or may be learned by practice. The advantages will be realized and attained by means of the elements and combinations particularly pointed out in the appended claims.

BRIEF DESCRIPTION OF THE DRAWINGS

The accompanying drawings, which are incorporated in and constitute a part of this specification, illustrate embodiments and together with the description, serve to explain the principles of the methods and systems.

DETAILED DESCRIPTION

Figure 1:
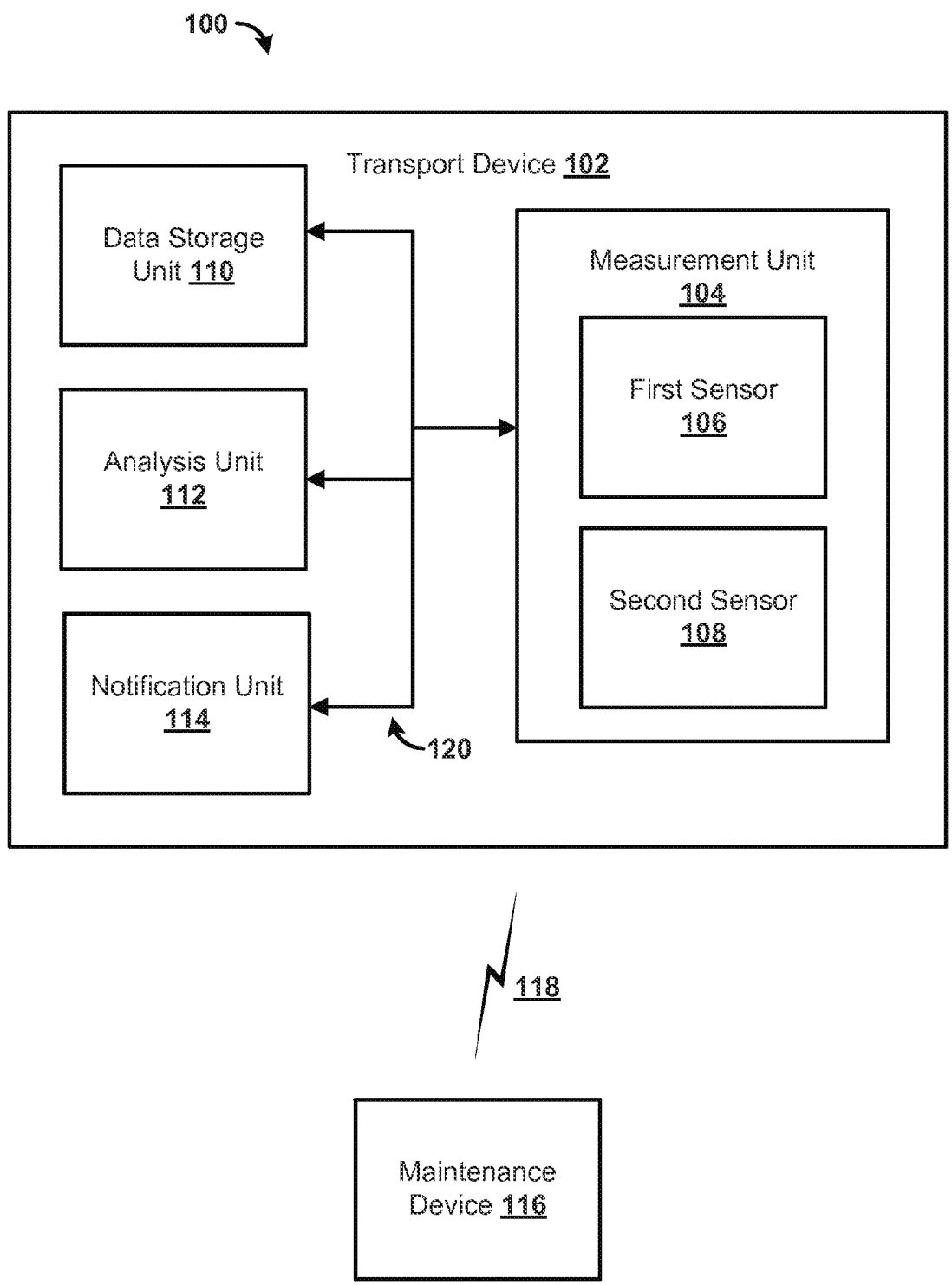
FIG. 1 is a block diagram illustrating an example system for detecting aerosols.

Before the present methods and systems are disclosed and described, it is to be understood that the methods and systems are not limited to specific methods, specific components, or to particular implementations. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems may be understood more readily by reference to the following detailed description of preferred embodiments and the examples included therein and to the Figures and their previous and following description.

As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium.

More particularly, the present methods and systems may take the form of web-implemented computer software. Any suitable computer-readable storage medium may be utilized including hard disks, CD-ROMs, optical storage devices, or magnetic storage devices.

Embodiments of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

Provided are methods and systems for warning a transport device, such as an aircraft (e.g., fixed wing or rotor) of potentially hazardous concentrations of ambient aerosols (e.g., aerosol particles) in the surrounding environment. Examples of ambient aerosols can comprise volcanic ash, smoke, soil, sand, and the like. An example system can function on-board a transport device and warn the crew of increasing concentrations of potentially hazardous concentrations of ambient aerosols. Thus, the crew of the transport device can steer the transport device away from an encountered plume prior to the transport device encountering high concentrations in the heart of the plume. While described primarily with regard to volcanic ash, the methods and systems provided are applicable to other aerosols, including but not limited to smoke, soil, sand, and the like. In one aspect, volcanic ash can comprise rock shards, sharp volcanic glass, and the like emitted during or after a volcanic eruption that can damage all forms of aircraft. The jagged exterior of volcanic ash can harm (e.g., by collisions, friction, and the like) aircraft engine components, rotors, windscreens, external lights, paint, any moving parts exposed to an unfiltered airflow, and the like. In one aspect, ash can melt in the high temperatures experienced inside a jet engine. In some scenarios, the melted ash can coat the interior of an engine and block cooling vents on turbine engine blades causing engines to shut down during flight. The concentration and composition of ash particles present in the air surrounding the transport device can determine how much and what type of damage could be done to the transport device. Therefore, the present methods and systems can be configured to rapidly detect the edge of a volcanic plume (e.g., where ash is present in lower concentrations than in the heart of the plume) in order to change course and steer away from the plume.

In one aspect, the present methods and systems can be configured to warn the transport device's crew of increasing concentrations of ambient aerosols with enough time to exit a plume before encountering the higher, more hazardous, concentrations in the center of the plume. The present methods and systems can be configured to operate in most conditions, including in clouds and at night, when many other techniques for detecting plumes fail. In an aspect, present methods and systems can discriminate between high concentrations of large ambient aerosols and high concentrations of smaller, anthropogenic aerosols and naturally-produced non-volcanic ash particles. In a further aspect, the methods and systems provided can record ash concentrations so that well-informed maintenance decisions based on ash exposure may be made.

In one aspect, the present methods and systems can be performed real-time. The methods and systems can be integrated on-board the aircraft and can sample air either being brought on-board through existing non-filtered air handling systems or through an inlet that pierces the aircraft skin.

In an exemplary embodiment, the methods and systems disclosed can be located within one or more measurement unit, analysis unit, data storage unit, and notification unit. For example, the measurement unit can comprise one or more sensors configured to measure concentration and size of ambient aerosols as well as determine composition of the ambient aerosols. The analysis unit can be configured to compare the concentration and size to one or more thresholds. The analysis unit can also determine whether composition information matches certain ambient aerosols. In response to the comparison to various thresholds, the notification unit can provide one or more notifications to a user (e.g., pilot, driver, air traffic control person) indicating potential danger due to ambient aerosols.

In summary, the present methods and systems can provide a unique and quick on-board method for detecting when a transport device encounters a volcanic ash plume and warning the crew before the transport device gets deep into the plume. The present methods and systems can conduct in situ sampling instead of relying solely on visual, satellite, seismic monitoring, or knowledge of current volcanic activity. The present methods and systems can be utilized under all conditions, such as during day, night, in-cloud, out-of-cloud, and the like. In one aspect, notifications of the conditions can be delivered directly to the crew and/or also to a remote station.

FIG. 1 is a block diagram illustrating an example system 100 for detecting aerosols. In one aspect, the system 100 can comprise a transport device 102. For example, the transport device 102 can comprise a vehicle, such as an aircraft.

In one aspect, the transport device 102 can comprise a measurement unit 104. For example, the measurement unit 104 can comprise instruments, sensors, and/or other devices configured to detect aerosols. Incoming, aerosol-laden air can be provided to the measurement unit 104. In one aspect, the measurement unit 104 can be configured to determine the size, quantity, concentration, and/or other information about incoming aerosols.

In one aspect, the measurement unit 104 can comprise one or more sensors. For example, the sensors can be configured to detect aerosols. In some aspects, the sensors can be combined into a single device, while in other aspects the sensors can be separated into multiple devices.

In one aspect, the measurement unit 104 can comprise a first sensor 106. The first sensor 106 can be configured to receive an air sample and determine the concentrations and sizes of particles in the ambient air, if any. For example, the first sensor 106 can comprise a modified optical particle counter configured for determining the concentrations and sizes of ambient aerosols. For example, the modified particle counter can be miniaturized and modified to allow the particles counted to pass through the instrument and into the next instrument for further analysis (e.g., instead of being stopped by an internal filter in the optical particle counter). In one aspect, the first sensor 106 can be configured to make measurements without removing the aerosols from the airstream. In one aspect, the first sensor 106 can be further configured to allow the aerosols to pass through instead of collecting the aerosols.

In one aspect, the measurement unit 104 can comprise a second sensor 108. The second sensor 108 can be configured to receive the ambient aerosols and determine whether the chemical composition of the ambient aerosols is consistent with that of an aerosol that poses a threat to safety or convenience of operation of the transport device 102. For example, a threat could be the presence of volcanic ash. As an example, the second sensor 108 can comprise an aethalometer, visible or infrared wavelength spectrometer, x-ray spectrometer, and/or the like. As a further example, the second sensor 108 can comprise a multi-wavelength aethalometer, which is an instrument configured to measure optical absorption as a function of wavelength.

In one aspect, the transport device 102 can comprise a data storage unit 110. The data storage unit 110 can be configured to record aerosol concentrations for quantifying aircraft exposure to these quantities during an aerosol plume encounter. In one aspect, the data storage unit 110 can be configured to record concentrations as a function of time. This data can provide maintenance teams with data needed for determining at what aerosol levels require enhanced maintenance to the transport device 102. This data can also be presented to the pilot in real-time to assist in determining ash hazard reduction techniques, such as turning off one or more engines so as to minimize damage and so that the minimum power required to get the aircraft from just outside the location of its ash encounter to a safe landing at an airport can be applied.

In one aspect, the transport device 102 can comprise an analysis unit 112. In an aspect, the analysis unit 112 can be configured to determine if the concentration of large aerosols exceeds a predetermined concentration threshold (e.g., threshold-of-concern). The predetermined concentration threshold can be set and adjusted by a user, or automatically based on aircraft location and likelihood of encountering a specific type of aerosol. In one aspect, the analysis unit 112 can be configured to determine if the concentration of any particular size aerosol exceeds a predetermined concentration threshold. If the threshold is exceeded, a perceptible alarm warning of a potential threat can be initiated and the second sensor 108 can be triggered. The second sensor 108 can record composition information about the aerosols. Then, the analysis unit 112 can determine if the composition information is consistent with volcanic ash, or any other type of aerosol. If the second sensor 108 determines that the plume is composed of volcanic ash (e.g., or any other aerosol that poses a threat to aircraft safety or convenience), the transport device 102 can initiate a perceptible imminent threat warning. Otherwise, the transport device 102 can remain at the caution alarm stage.

In one aspect, the first sensor 106 can provide a variety of measurements to the analysis unit 112. For example, the first sensor 106 can provide concentration and size measurements to the analysis unit 112. Alternatively, the first sensor 106 can provide raw measurement data to the analysis unit 112, and the analysis unit 112 can determine or more concentration or size based on the raw data. The analysis unit 112 can thus determine if there are high concentrations of a particular size particle in the atmosphere surrounding the aircraft. Aerosols from natural sources, such as volcanic ash, forest fire smoke, and soil dust, tend to be larger in size than anthropogenic aerosols. Thus, any large aerosols are more likely to be from a natural source. Because large aerosols fall out of the atmosphere more quickly than small aerosols, high concentrations of large aerosols mean that the transport device 102 is close to a large source of these aerosols, such as a volcanic eruption or haboob. If the concentration of large aerosols reaching the first sensor 106 exceeds a predetermined threshold, one or more notifications (e.g., alarms) can be triggered. In one aspect, the analysis unit 112 can be configured to activate the second sensor 108 if the size and/or concentration of ambient aerosols exceed one or more thresholds.

In another aspect, the analysis unit 112 can be configured to receive composition information from the second sensor 108. The analysis unit 112 can be configured to determine whether the composition information matches corresponding composition information for one or more ambient aerosols, such as volcanic ash. For example, analysis unit 112 can be configured to compare the composition information to signature data. In one aspect, the signature data can be characteristic of one or more specified aerosols. For example, the analysis unit 112 can be configured to generate an expected composition of the ambient aerosols as a function of time. The analysis unit 112 can compare the expected composition as a function of time to the measured composition as a function of time. The analysis unit 112 can be configured to determine if the expected composition diverges from the measured composition. In one aspect, the analysis unit 112 can be configured to determine a rate of divergence in order to determine a level of potential harm to the transport device 102.

In an aspect, the predetermined concentration threshold for volcanic ash can be a concentration of about 1, 2, 3, 4, 5, 6, 7, 8, 9, 10 mg/m3 and the like. Other concentrations are contemplated and can vary for different aerosols. By way of example, concentrations established by standard setting bodies and other organizations can be utilized, such as those provided by the International Volcanic Ash Task Force, International Civil Aviation Organisation (ICAO), the United States Air Force Research Laboratory, and the like. In another aspect, multiple thresholds can be used to classify concentrations (e.g., low, medium, high). For example, the provided methods and systems can utilize low (e.g., less than about 2 mg/m3), medium (e.g., less than about 4 mg/m3), and high (e.g., greater than about 4 mg/m3) thresholds.

A size threshold can be applied to assist classification of a particular aerosol. For example, about 2.5 microns can be used as the dividing point between large and small aerosols, with particles between about 2.5 and about 10 microns being referred to as the coarse fraction. ICAO uses 10 microns as the size of ash that can stay in the atmosphere for days and impact aircraft. For example, a 20 micron ash particle injected into the atmosphere at 10 km can take approximately 10 days to reach the ground. Other examples of aerosol sizes that can be used to classify an aerosol are shown below in Table 1 (see "Atmospheric Physics and Chemistry," Seinfeld and Pandis, (1998), specifically incorporated herein in its entirety):

TABLE 1

| Source | Estimated Flux (Tg yr$^{-1}$) | | | Particle Size Category* |
|---|---|---|---|---|
| | Low | High | Best | |
| NATURAL Primary | | | | |
| Soil Dust (mineral aerosol) | 1000 | 3000 | 1500 | Mainly coarse |
| Sea salt | 1000 | 10000 | 1300 | Coarse |
| Volcanic dust | 4 | 10000 | 30 | Coarse |
| Biological debris | 26 | 80 | 50 | Coarse |
| Secondary | | | | |
| Sulfates from biogenic gases | 80 | 150 | 130 | Fine |
| Sulfates from volcanic SO$_2$ | 5 | 60 | 20 | Fine |
| Organic matter from biogenic VOC | 40 | 200 | 60 | Fine |
| Nitrates from NO$_x$ | 15 | 50 | 30 | Fine and coarse |
| Total natural | 2200 | 23500 | 3100 | |
| ANTHROPOGENIC Primary | | | | |
| Industrial dust, etc. (except soot) | 40 | 130 | 100 | Fine and coarse |
| Soot | 5 | 20 | 10 | Mainly fine |
| Secondary | | | | |
| Sulfates from SO$_2$ | 170 | 250 | 190 | Fine |
| Biomass burning | 60 | 150 | 90 | Fine |
| Nitrates from NO$_x$ | 25 | 65 | 50 | Mainly coarse |
| Organics from anthropogenic VOC | 5 | 25 | 10 | Fine |
| Total anthropogenic | 300 | 650 | 450 | |
| Total | 2500 | 24000 | 3600 | |

In one aspect, the transport device 102 can comprise a notification unit 114. In one aspect, the notification unit 114 can be configured to provide one or more notifications, such as alarms, signals, messages, indicators, and the like. For example, the notification unit 114 can be configured to provide a first notification. The first notification can be provided based on an instruction from the analysis unit 112 to provide the first notification. In one aspect, the first notification can comprise a caution notification. For example, the first notification can be provided if the concentration of ambient aerosols exceeds a first threshold and/or if the size of the ambient aerosols exceeds a second threshold. As another example, the notification unit 114 can be configured to provide a second notification. The second notification can comprise a volcanic ash warning alarm. For example, the second notification can be provided if the composition information matches the composition of volcanic ash within a specified threshold. For example, the specified threshold can indicate that a silicon-to-aluminum ratio is greater than 1.5. Another example could be a silicon concentration, such as 50 micrograms per cubic meter of air. In another aspect, the threshold can be based on a 4 milligram per cubic meter 'high' threshold. However, a variety of different ratios, concentration, and other values can be used as the specified threshold. In one aspect, if the composition information from the second sensor 108 results in a determination, within a specified level of confidence (e.g., by comparison to the threshold), that the aerosols impacting the transport device 102 are volcanic ash or other aerosol that impacts safety or convenience, then the analysis unit 112 can instruct the notification unit 114 to provide the second notification.

In one aspect, the system 100 can comprise a maintenance device 116. For example, the maintenance device 116 can be configured to provide maintenance to the transport device 102. As another example, the maintenance device 116 can be configured to detect potential maintenance needs for the transport device 102. For example, the maintenance device 116 can be configured to communicate with the transport device 102 through a communication link 118, such as a wireless link or hardwire link. For example, the maintenance device 116 can be configured to access information stored in the data storage unit 110. In one aspect, the maintenance device 116 can be configured to determine an amount of aerosol particle accumulation (e.g., volcanic ash accumulation) in at least a portion (e.g., an engine) of the transport device. In one aspect, the maintenance device 116 can be configured to provide a notification indicating that the portion of the transport device 102 with the accumulation is due for maintenance (e.g., cleaning, replacement, repair).

In one aspect, the transport device 102 can comprise an internal bus 120 configured to carry information throughout the transport device 102. For example, information from the first sensor 106 and second sensor 108 can be provided to the data storage unit 110 and/or analysis unit 112 through the internal bus 120. Additionally, the notification unit 114 can receive information and/or instructions from the analysis unit 112 as the basis of one or more notifications provided by the notification unit 114.

Figure 2:
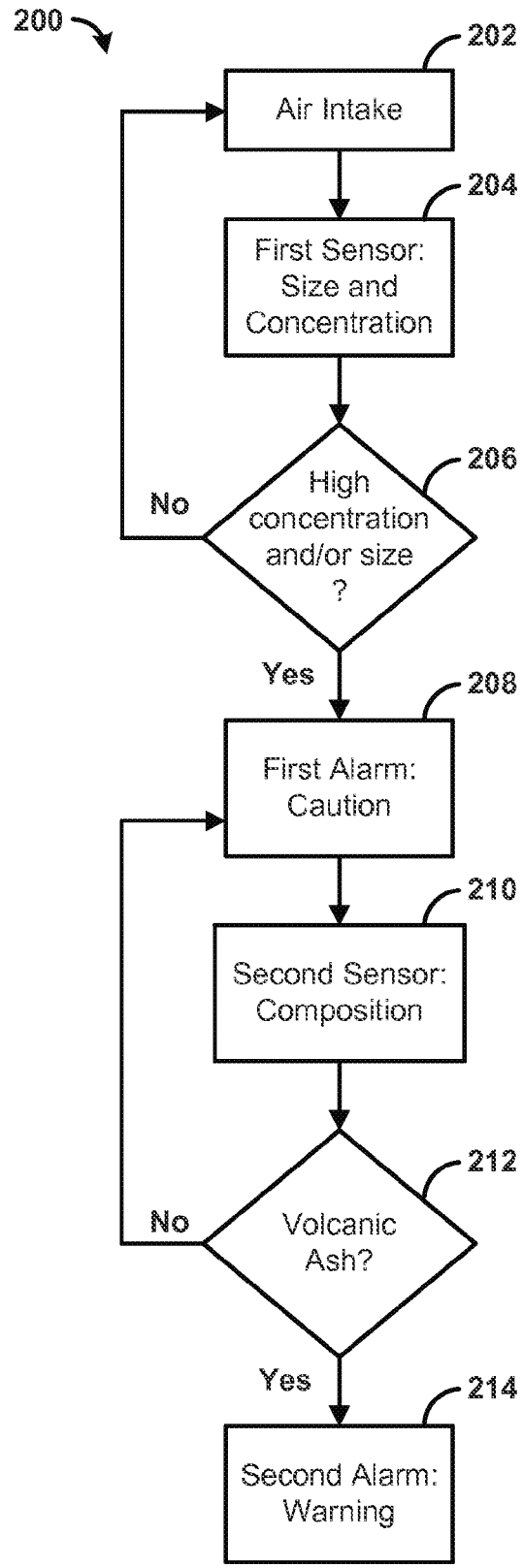
FIG. 2 is a block diagram illustrating an example process for detecting ambient aerosols.

FIG. 2 is a block diagram illustrating an exemplary process 200 for detecting ambient aerosols in a system. The system can comprise sensors, alarms, data processing devices, and the like. The process 200 can comprise, for example, measurements, decisions, and resulting alarms that can be implemented. In an aspect, various alarm conditions can be implemented with varying colors, sounds, and tactile sensations associated therewith.

At step 202, an air sample can be received. In an aspect, ambient air from outside the aircraft can be drawn from pre-existing air intakes on the aircraft provided that the air intakes are not filtered prior to the air being drawn into this system. This intake method can avoid the requirement of FAA certification. If this option is not available on an aircraft, an inlet tube can be installed to bring the ambient air into the aircraft. In an aspect, the air can be drawn through the system using a small air pump to control the flow rate through the system.

At step 204, a concentration and size of ambient aerosols in the air sample can be measured by a first sensor. At step 206, it can be determined whether a size and/or concentration of ambient aerosols in the air sample exceeds one or more predetermined thresholds. If the size and/or concentration of ambient aerosols exceeds the one or more predetermined thresholds, then the process 200 can proceed to step 208. Otherwise, the process 200 can return to step 202. At step 208, a first alarm can be provided. For example, the first alarm can be a caution alarm to a pilot of transport device, such as an aircraft. At step 210, a second sensor can perform one or more measurements of the composition of aerosols in the air sample. At step 212, it can be determined if the ambient aerosols are aerosols that pose a threat to travel safety or convenience. For example, it can be determined if the ambient aerosols comprise volcanic ash. If it is determined that the composition of the ambient aerosols pose a threat to travel safety or convenience, the process 200 can proceed to step 214. Otherwise, the process 200 can return to step 208, or other step, such as step 202. At step 214, a second alarm can be triggered. For example, the second alarm can be a volcanic ash warning. The first and second alarms can comprise one or more of audible, visual, and/or tactile signals. For example, the first alarm (e.g., caution alarm) can be yellow and coupled with an audible alarm. As another example, the second alarm (e.g., volcanic ash warning alarm) can be red and coupled with an audible alarm that can be differentiated from the first alarm.

Figure 3:
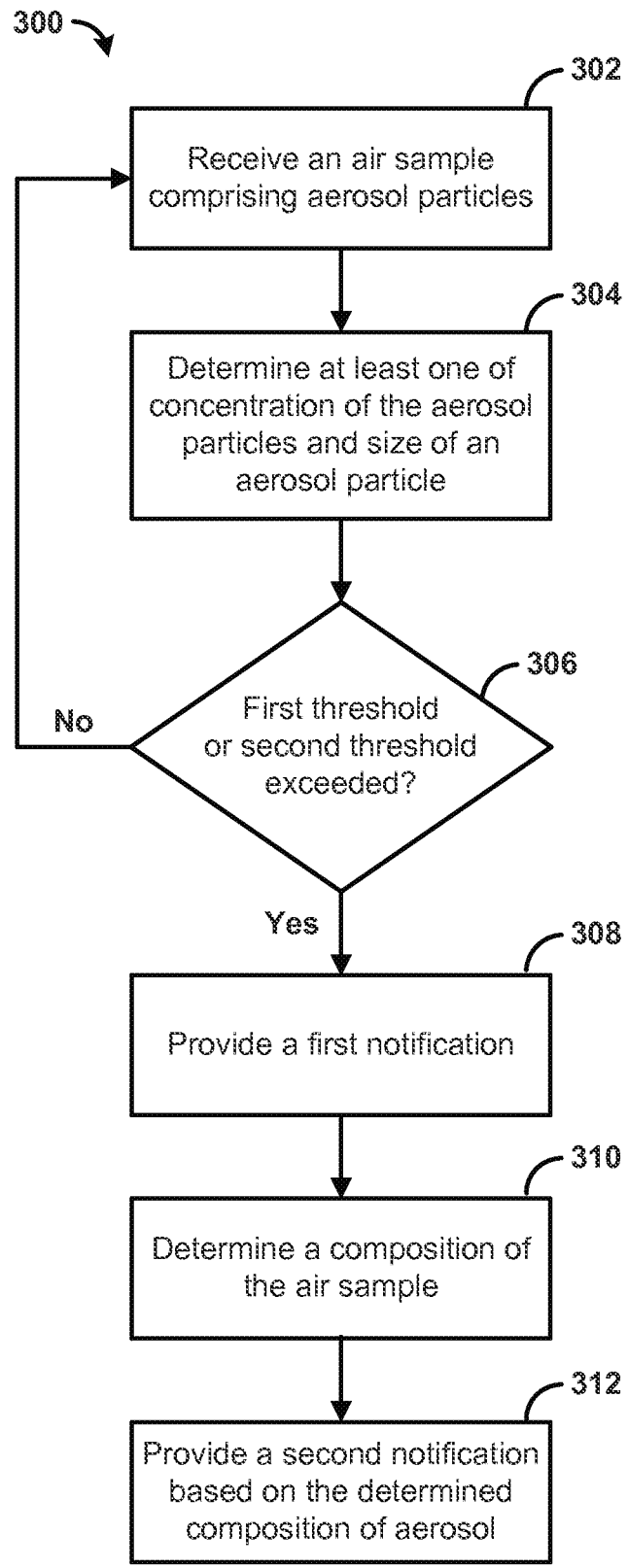
FIG. 3 is a flowchart illustrating an example method for detecting ambient aerosols.

FIG. 3 is a flowchart illustrating an example method 300 for detecting ambient aerosols. At step 302, an air sample comprising aerosol particles can be received. For example, the aerosol particles can comprise at least one of volcanic ash, smoke, soil, and sand. At step 304, at least one of concentration of the aerosol particles and size of an aerosol particle from the aerosol particles can be determined. For example, step 304 can be accomplished by an optical particle counter.

At step 306, the method can determine if at least one of the concentration of aerosol particles exceeds the first predetermined threshold and size of an aerosol particle from the aerosol particles exceeds the second predetermined threshold. If at least one of the concentration of aerosol particles exceeds the first predetermined threshold and size of an aerosol particle from the aerosol particles exceeds the second predetermined threshold, then the method 300 can proceed to step 308. Otherwise, the method 300 can proceed to step 302. At step 308, a first notification (e.g. caution notification, additional notification) can be provided. For example, the first notification can be provided as a warning in an aircraft cockpit. In one aspect, the first notification can be a caution warning.

At step 310, a composition of the air sample can be determined based on the determined composition of the aerosol. For example, the composition of the aerosol can be determined by one or more aethalometer, visible or infrared wavelength spectrometer, x-ray spectrometer, and/or the like. As a further example, a multi-wavelength aethlometer can measure optical absorption as a function of wavelength. The composition of the aerosol can indicate at least a part of the composition of the air sample. For example, the air sample can comprise a variety of different aerosol particles.

At step 312, a second notification can be provided based on the determined composition of the air sample. In one aspect, the second notification can indicate the presence of volcanic ash. In one aspect, the second notification can be a pilot perceptible warning. For example, the second notification can be provided as a warning in an aircraft cockpit. In one aspect, the second notification can be a volcanic ash warning. In another aspect, the second notification can be provided if it is determined that the aerosol poses an impact on at least one of aircraft travel safety and aircraft travel convenience. In one aspect, the first notification and/or second notification can be sent to a remote location, such as an air traffic control station, a fleet management station, another transport device, a weather station, and/or the like.

Figure 4:
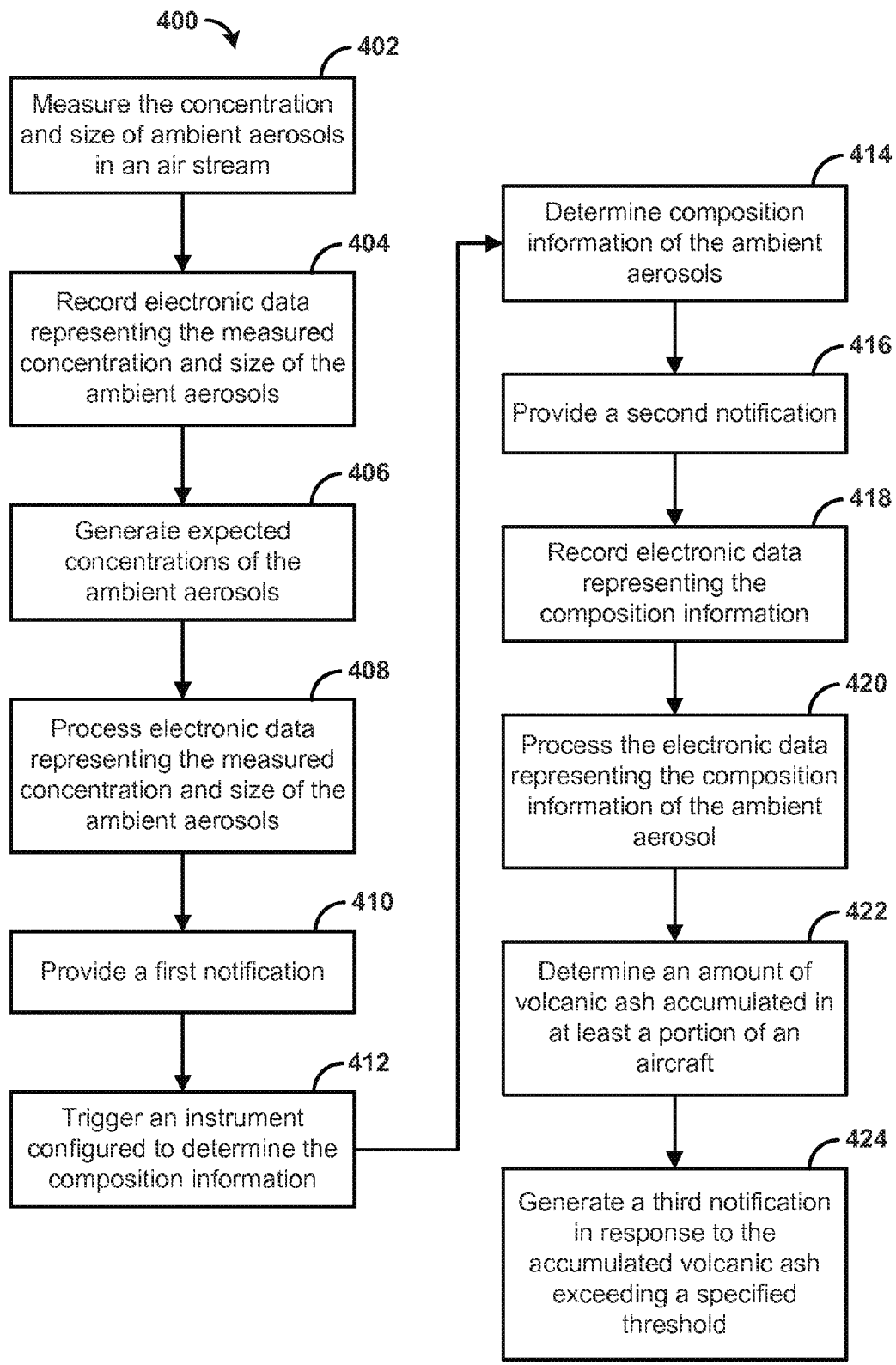
FIG. 4 is a flowchart illustrating another example method for detecting ambient aerosols.

FIG. 4 is a flowchart illustrating another example method 400 for detecting ambient aerosols. At step 402, concentration and size of ambient aerosols in an air stream can be measured. For example, the concentration and size of the ambient aerosols can be measured by an optical particle counter. For example the optical particle counter can detect ambient aerosols through light scattering, light obscuration, direct imaging, and/or other similar particle counting and measurement techniques.

At step 404, electronic data representing the measured concentration and size of the ambient aerosols can be recorded. For example, measured concentrations of the ambient aerosols can be stored in memory. For example, the measured concentrations can be stored as a function of time. In one aspect, the measured concentrations can be stored if the composition information indicates the presence of volcanic ash in the air stream.

At step 406, expected concentrations of the ambient aerosols can be generated. For example, the expected concentrations can be generated as a function of time. In one aspect, the expected concentrations can be generated in memory. At step 408, the electronic data representing the measured concentration and size of the ambient aerosols can be processed. For example, the measured concentration of ambient aerosols can be compared with a corresponding respective expected concentration of ambient aerosols. For example, the measured concentration and the expected concentration can be compared as functions of time.

At step 410, a first notification can be provided. For example, the first notification can be provided if at least one of the size of the ambient aerosols exceeds a first threshold and the concentration of the ambient aerosols exceeds a second threshold. As another example, the first notification can be generated in response to the measured concentration matching (e.g., within a specified threshold) the corresponding respective expected concentration. In one aspect, providing the first notification can comprise generating an electronic signal that triggers a perceptible caution alarm if at least one of the portion of the electronic data representing the measured concentration exceeds the first threshold and the portion of the electronic data representing the size of the ambient aerosol exceeds the second threshold.

At step 412, an instrument configured to determine the composition information can be triggered if at least one of a portion of the electronic data representing the measured concentration exceeds the first threshold and a portion of the electronic data representing the size of the ambient aerosol exceeds the second threshold. At step 414, composition information of the ambient aerosols can be determined. In one aspect, determining the composition information of the ambient aerosols occurs if at least one of the size of the ambient aerosols exceeds the first threshold and the concentration of the ambient aerosols exceeds the second threshold.

At step 416, a second notification can be provided. For example, the second notification can be provided if the composition information indicates presence of volcanic ash in the air stream. In one aspect, providing the second notification can comprise generating an electronic signal that triggers a perceptible volcanic ash warning alarm if the electronic data representing the composition of the ambient aerosol matches the signature data for volcanic ash within a user-specified confidence level. In one aspect, the first notification and second notification are at least one of audible in a cockpit of an aircraft and visible in the cockpit of the aircraft.

At step 418, electronic data representing the composition information of the ambient aerosols can be recorded. For example, the electronic data can be stored locally and/or remotely in one or more databases. In one aspect, the electronic data can record the composition information as a function of time. At step 420, the electronic data representing the composition information of the ambient aerosol can be processed. For example, the composition information can be compared to other data, such as signature data for volcanic ash or other particles. The composition information can normalized, rounded, truncated, adjusted, and/or otherwise modified for further analysis.

At step 422, an amount of volcanic ash accumulated in at least a portion of an aircraft can be determined. For example, the volcanic ash can accumulate over time in a portion of the aircraft, such as an engine of the aircraft. In one aspect, the amount of volcanic ash accumulated can be based on direct measurement, such as through a maintenance device when the aircraft is stationary. In another aspect, the amount of volcanic ash accumulated can be determined based on the electronic data. For example, the concentration measured as a function of time can indicate (e.g., for estimation purposes) the amount of volcanic ash accumulated on the portion of the aircraft.

At step 424, a third notification (e.g., perceptible alarm) can be generated in response to the accumulated volcanic ash exceeding a specified threshold. For example, the specified threshold can indicate a silicon-to-aluminum ratio greater than 1.5. Another example could be a silicon concentration, such as 50 micrograms per cubic meter of air. In another aspect, the specified threshold can be based on a 4 milligram per cubic meter 'high' threshold. In one aspect, the third notification can comprise an audible alarm, light indicator, an electronic message, and/or the like. The notification can be provided through a flight system in a cockpit, to a portable electronic device, and/or the like. For example, the notification can be provided to or generated on a maintenance device.

Figure 5:
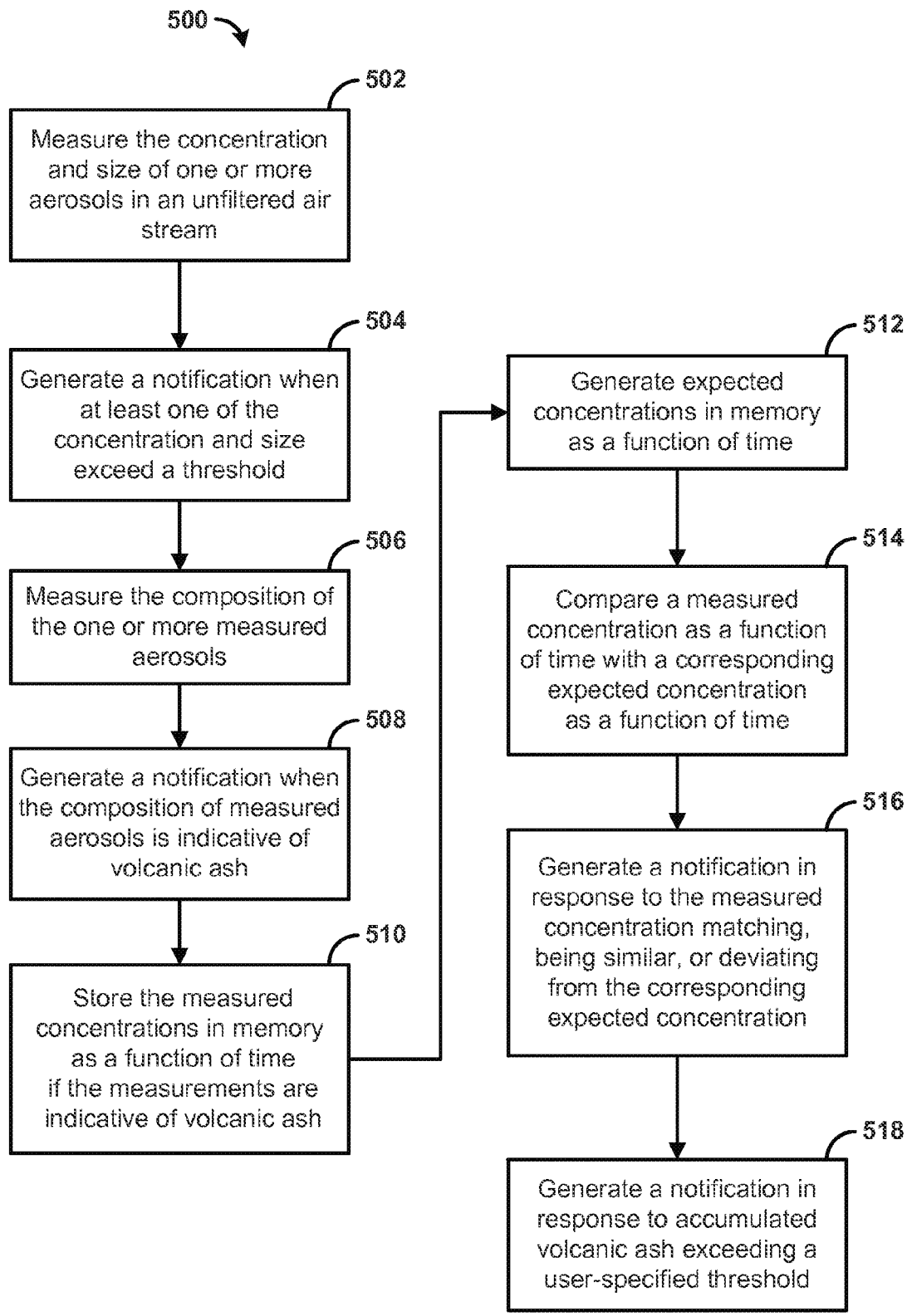
FIG. 5 is a flowchart illustrating yet another method for detecting ambient aerosols.

FIG. 5 is a flowchart illustrating yet another method 500 for detecting ambient aerosols. In another aspect, the method 500 can be used to detect an aircraft approaching a volcanic plume, steer an aircraft away from a volcanic plume, and assist in volcanic ash maintenance for an aircraft.

At step 502, the concentration and size of one or more aerosols can be measured in an unfiltered air stream encountered by an aircraft through a first detector. In one aspect, the first detector can comprise an optical particle counter. For example, the concentration and size of one or more aerosols can be measured by the optical particle counter. For example the optical particle counter can detect ambient aerosols through light scattering, light obscuration, direct imaging, and/or similar particle counter and measurement techniques.

At step 504, a notification (e.g., perceptible caution alarm) can be generated when at least one of the concentration and size of the one or more measured aerosols exceeds a respective user-specified threshold. For example, the notification can comprise an audible alarm, light indicator, an electronic message, and/or the like. The notification can be provided through a flight system in a cockpit, to a portable electronic device, and/or the like. At step 506, the composition of the one or more measured aerosols out of the first detector can be measured through a second detector. For example, the composition of the one or more measured aerosols out of the first detector can be determined by one or more aethalometer, visible or infrared wavelength spectrometer, x-ray spectrometer, and/or the like. As a further example, a multi-wavelength aetholometer can measure optical absorption as a function of wavelength.

At step 508, a notification (e.g., perceptible warning alarm) can be generated when the composition of the one or more measured aerosols is indicative with volcanic ash with a user-specified confidence level. For example, the notification can comprise an audible alarm, light indicator, an electronic message, and/or the like. The notification can be provided through a flight system in a cockpit, to a portable electronic device, and/or the like. In one aspect, the notification can be sent to a remote location, such as an air traffic control station, a fleet management station, another transport device, a weather service, and the like. At step 510, measured concentrations can be stored in memory as a function of time if the measurements are consistent with volcanic ash. For example, the measured concentrations can be stored locally and/or remotely in one or more databases. At step 512, expected concentrations can be generated in memory as a function of time. For example, the expected concentrations can be generated at a previous time or in real-time as the aerosols are being measured. The expected concentrations can be based on previous data indicative of flight conditions with or without volcanic ash or other particles.

At step 514, the respective measured concentration as a function of time can be compared with a corresponding respective expected concentration as a function of time. For example, the measured concentration at a first time can be compared with an expected concentration associated with the first time. This comparison can be repeated over time to identify if the measured concentration is becoming increasingly greater and/or less than the expected concentration. At step 516, a notification (e.g., perceptible alarm) can be generated in response to the measured concentration as a function of time matching, being similar, or deviating from the corresponding respective expected concentration as a function of time to a user-specified degree. For example, the notification can comprise an audible alarm, light indicator, an electronic message, and/or the like. The notification can be provided through a flight system in a cockpit, to a portable electronic device, and/or the like.

At step 518, a notification (e.g., perceptible alarm) can be generated in response to the accumulated volcanic ash determined exceeding a user-specified threshold. For example, the notification can comprise an audible alarm, light indicator, an electronic message, and/or the like. The notification can be provided through a flight system in a cockpit, to a portable electronic device, and/or the like. For example, the notification can be provided to or generated on a maintenance device. In one aspect, the user-specified threshold can indicate a silicon-to-aluminum ratio greater than 1.5. Another example could be a silicon concentration, such as 50 micrograms per cubic meter of air. In another aspect, the threshold can be based on a 4 milligram per cubic meter 'high' threshold.

Figure 6:
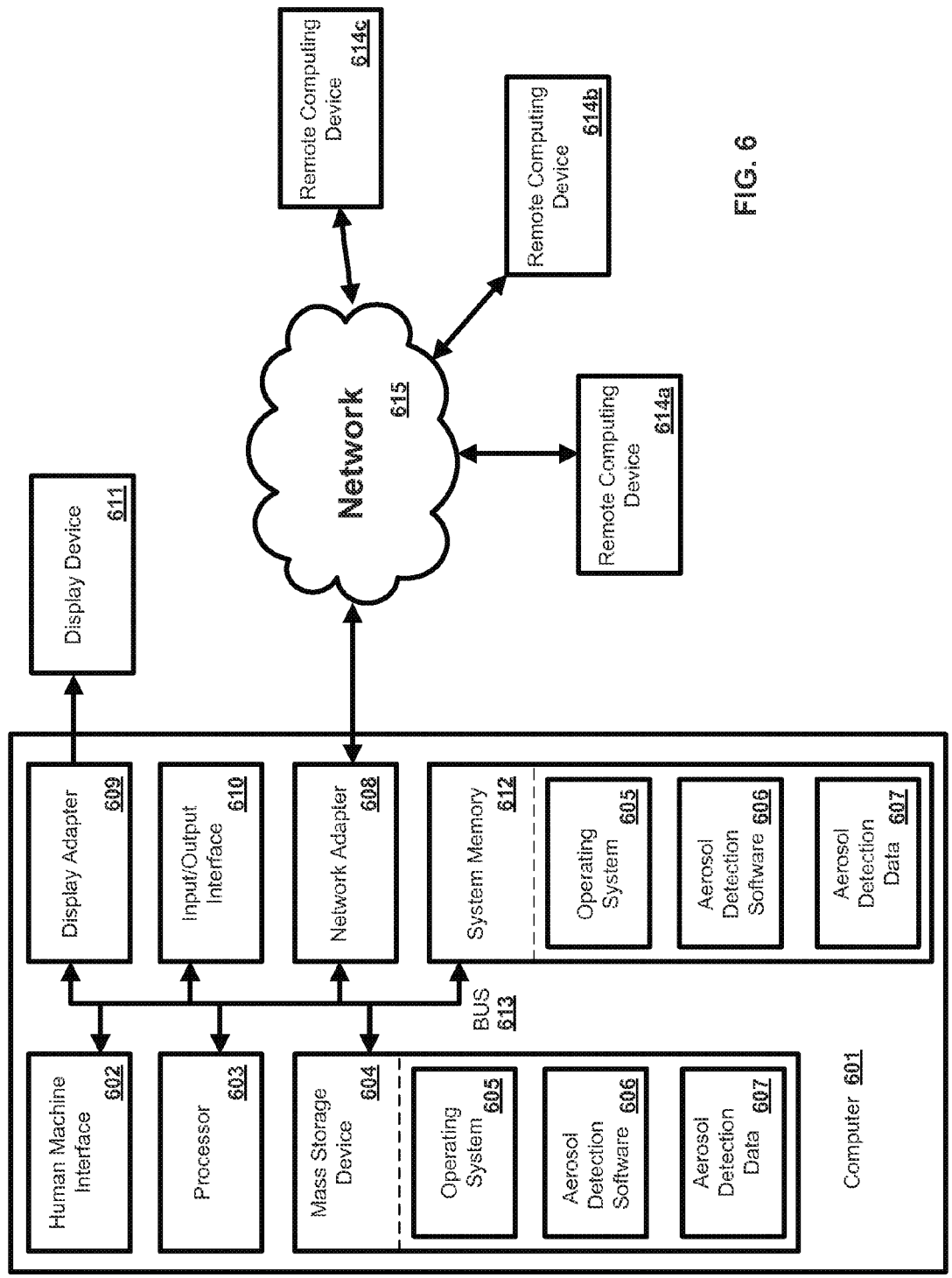
FIG. 6 is a block diagram illustrating an example computing system in which the present methods and systems can operate.

In an exemplary aspect, the methods and systems can be implemented on a computer 601 as illustrated in FIG. 6 and described below. By way of example, analysis unit 112 and/or notification unit 114 of FIG. 1 can be a computer as illustrated in FIG. 6. Similarly, the methods and systems disclosed can utilize one or more computers to perform one or more functions in one or more locations. FIG. 6 is a block diagram illustrating an exemplary operating environment for performing the disclosed methods. This exemplary operating environment is only an example of an operating environment and is not intended to suggest any limitation as to the scope of use or functionality of operating environment architecture. Neither should the operating environment be interpreted as having any dependency or requirement relating to any one or combination of components illustrated in the exemplary operating environment.

The present methods and systems can be operational with numerous other general purpose or special purpose computing system environments or configurations. Examples of well known computing systems, environments, and/or configurations that can be suitable for use with the systems and methods comprise, but are not limited to, personal computers, server computers, laptop devices, and multiprocessor systems. Additional examples comprise set top boxes, programmable consumer electronics, network PCs, minicomputers, mainframe computers, distributed computing environments that comprise any of the above systems or devices, and the like.

The processing of the disclosed methods and systems can be performed by software components. The disclosed systems and methods can be described in the general context of computer-executable instructions, such as program modules, being executed by one or more computers or other devices. Generally, program modules comprise computer code, routines, programs, objects, components, data structures, etc. that perform particular tasks or implement particular abstract data types. The disclosed methods can also be practiced in grid-based and distributed computing environments where tasks are performed by remote processing devices that are linked through a communications network. In a distributed computing environment, program modules can be located in both local and remote computer storage media including memory storage devices.

Further, one skilled in the art will appreciate that the systems and methods disclosed herein can be implemented via a general-purpose computing device in the form of a computer 601. The components of the computer 601 can comprise, but are not limited to, one or more processors or processing units 603, a system memory 612, and a system bus 613 that couples various system components including the processor 603 to the system memory 612. In the case of multiple processing units 603, the system can utilize parallel computing.

The system bus 613 represents one or more of several possible types of bus structures, including a memory bus or memory controller, a peripheral bus, an accelerated graphics port, and a processor or local bus using any of a variety of bus architectures. By way of example, such architectures can comprise an Industry Standard Architecture (ISA) bus, a Micro Channel Architecture (MCA) bus, an Enhanced ISA (EISA) bus, a Video Electronics Standards Association (VESA) local bus, an Accelerated Graphics Port (AGP) bus, and a Peripheral Component Interconnects (PCI), a PCI-Express bus, a Personal Computer Memory Card Industry Association (PCMCIA), Universal Serial Bus (USB) and the like. The bus 613, and all buses specified in this description can also be implemented over a wired or wireless network connection and each of the subsystems, including the processor 603, a mass storage device 604, an operating system 605, aerosol detection software 606, aerosol detection data 607, a network adapter 608, system memory 612, an Input/Output Interface 610, a display adapter 609, a display device 611, and a human machine interface 602, can be contained within one or more remote computing devices 614a,b,c at physically separate locations, connected through buses of this form, in effect implementing a fully distributed system.

The computer 601 typically comprises a variety of computer readable media. Exemplary readable media can be any available media that is accessible by the computer 601 and comprises, for example and not meant to be limiting, both volatile and non-volatile media, removable and non-removable media. The system memory 612 comprises computer readable media in the form of volatile memory, such as random access memory (RAM), and/or non-volatile memory, such as read only memory (ROM). The system memory 612 typically contains data such as aerosol detection data 607 and/or program modules such as operating system 605 and aerosol detection software 606 that are immediately accessible to and/or are presently operated on by the processing unit 603.

In another aspect, the computer 601 can also comprise other removable/non-removable, volatile/non-volatile computer storage media. By way of example, FIG. 6 illustrates a mass storage device 604 which can provide non-volatile storage of computer code, computer readable instructions, data structures, program modules, and other data for the computer 601. For example and not meant to be limiting, a mass storage device 604 can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Optionally, any number of program modules can be stored on the mass storage device 604, including by way of example, an operating system 605 and aerosol detection software 606. Each of the operating system 605 and detection software 606 (or some combination thereof) can comprise elements of the programming and the detection software 606. Aerosol detection data 607 can also be stored on the mass storage device 604. Aerosol detection data 607 can be stored in any of one or more databases known in the art. Examples of such databases comprise, DB2®, Microsoft® Access, Microsoft® SQL Server, Oracle®, mySQL, PostgreSQL, and the like. The databases can be centralized or distributed across multiple systems.

In another aspect, the user can enter commands and information into the computer 601 via an input device (not shown). Examples of such input devices comprise, but are not limited to, a keyboard, pointing device (e.g., a "mouse"), a microphone, a joystick, a scanner, tactile input devices such as gloves, and other body coverings, and the like. These and other input devices can be connected to the processing unit 603 via a human machine interface 602 that is coupled to the system bus 613, but can be connected by other interface and bus structures, such as a parallel port, game port, an IEEE 1394 Port (also known as a Firewire port), a serial port, or a universal serial bus (USB).

In yet another aspect, a display device 611 can also be connected to the system bus 613 via an interface, such as a display adapter 609. It is contemplated that the computer 601 can have more than one display adapter 609 and the computer 601 can have more than one display device 611. For example, a display device can be a monitor, an LCD (Liquid Crystal Display), or a projector. In addition to the display device 611, other output peripheral devices can comprise components such as speakers (not shown) and a printer (not shown) which can be connected to the computer 601 via Input/Output Interface 610. Any step and/or result of the methods can be output in any form to an output device. Such output can be any form of visual representation, including, but not limited to, textual, graphical, animation, audio, tactile, and the like. The display 611 and computer 601 can be part of one device, or separate devices.

The computer 601 can operate in a networked environment using logical connections to one or more remote computing devices 614a,b,c. By way of example, a remote computing device can be a personal computer, portable computer, smartphone, a server, a router, a network computer, a peer device or other common network node, and so on. Logical connections between the computer 601 and a remote computing device 614a,b,c can be made via a network 615, such as a local area network (LAN) and/or a general wide area network (WAN). Such network connections can be through a network adapter 608. A network adapter 608 can be implemented in both wired and wireless environments. Such networking environments are conventional and commonplace in dwellings, offices, enterprise-wide computer networks, intranets, and the Internet.

For purposes of illustration, application programs and other executable program components such as the operating system 605 are illustrated herein as discrete blocks, although it is recognized that such programs and components reside at various times in different storage components of the computing device 601, and are executed by the data processor(s) of the computer. An implementation of aerosol detection software 606 can be stored on or transmitted across some form of computer readable media. Any of the disclosed methods can be performed by computer readable instructions embodied on computer readable media. Computer readable media can be any available media that can be accessed by a computer. By way of example and not meant to be limiting, computer readable media can comprise "computer storage media" and "communications media." "Computer storage media" comprise volatile and non-volatile, removable and non-removable media implemented in any methods or technology for storage of information such as computer readable instructions, data structures, program modules, or other data. Exemplary computer storage media comprises, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

The methods and systems can employ Artificial Intelligence techniques such as machine learning and iterative learning. Examples of such techniques include, but are not limited to, expert systems, case based reasoning, Bayesian networks, behavior based AI, neural networks, fuzzy systems, evolutionary computation (e.g. genetic algorithms), swarm intelligence (e.g. ant algorithms), and hybrid intelligent systems (e.g. Expert inference rules generated through a neural network or production rules from statistical learning).

While the methods and systems have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

Throughout this application, various publications are referenced. The disclosures of these publications in their entireties are hereby incorporated by reference into this application in order to more fully describe the state of the art to which the methods and systems pertain.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:

1. A method for detecting ambient aerosols, comprising:
measuring a concentration and a size of ambient aerosols in an air stream;
providing a first notification if at least one of the size of the ambient aerosols exceeds a first threshold and the concentration of the ambient aerosols exceeds a second threshold;
determining composition information of the ambient aerosols;
providing a second notification if the composition information indicates presence of volcanic ash in the air stream;
storing electronic data representing the measured concentration of the ambient aerosols in memory as a function of time if the composition information indicates the presence of volcanic ash in the air stream;
generating expected concentration of the ambient aerosols in memory as a function of time;
comparing the measured concentration of ambient aerosols as a function of time with corresponding respective expected concentration of ambient aerosols as a function of time; and
generating a perceptible alarm in response to the measured concentration as a function of time matching within a specified threshold the corresponding respective expected concentration as a function of time.

2. The method of claim 1, wherein determining the composition information of the ambient aerosols occurs if at least one of the size of the ambient aerosols exceeds the first threshold and the concentration of the ambient aerosols exceeds the second threshold.

3. The method of claim 1, further comprising:
recording electronic data representing the size of the ambient aerosols;
processing the electronic data representing the measured concentration of the ambient aerosols and the electronic data representing the size of the ambient aerosols; and
triggering an instrument configured to determine the composition information if at least one of a portion of the electronic data representing the measured concentration exceeds the first threshold and a portion of the electronic data representing the size of the ambient aerosol exceeds the second threshold.

4. The method of claim 3, further comprising:
storing electronic data representing the composition information of the ambient aerosols; and
processing the electronic data representing the composition information of the ambient aerosol,
wherein providing the first notification comprises generating an electronic signal that triggers a perceptible caution alarm if the at least one of the portion of the electronic data representing the measured concentration exceeds the first threshold and the portion of the electronic data representing the size of the ambient aerosol exceeds the second threshold, and
wherein providing the second notification comprises generating an electronic signal that triggers a perceptible volcanic ash warning alarm if the electronic data representing the composition of the ambient aerosol matches signature data for volcanic ash within a specified confidence level.

5. The method of claim 1, wherein the first notification and the second notification are at least one of audible in a cockpit of an aircraft and visible in the cockpit of the aircraft.

6. The method of claim 1, further comprising:
determining an amount of volcanic ash accumulated in at least a portion of an aircraft; and
generating a perceptible alarm in response to the accumulated volcanic ash exceeding a specified threshold.

7. A method for detecting ambient aerosols, comprising:
measuring a concentration and a size of ambient aerosols in an air stream;
recording electronic data representing the measured concentration and the size of the ambient aerosols;
processing the electronic data representing the measured concentration and size of the ambient aerosols;
providing a first notification if at least one of the size of the ambient aerosols exceeds a first threshold and the concentration of the ambient aerosols exceeds a second threshold, wherein providing the first notification comprises generating an electronic signal that triggers a perceptible caution alarm if at least one of the portion of the electronic data representing the measured concentration exceeds the first threshold and the portion of the electronic data representing the size of the ambient aerosol exceeds the second threshold;
triggering an instrument configured to determine composition information if the at least one of the portion of the electronic data representing the measured concentration exceeds the first threshold and the portion of the electronic data representing the size of the ambient aerosol exceeds the second threshold;
determining the composition information of the ambient aerosols;
recording electronic data representing the composition information of the ambient aerosols;
processing the electronic data representing the composition information of the ambient aerosol; and
providing a second notification if the composition information indicates presence of volcanic ash in the air stream, wherein providing the second notification comprises generating an electronic signal that triggers a perceptible volcanic ash warning alarm if the electronic data representing the composition of the ambient aerosol matches signature data for volcanic ash within a specified confidence level.

8. The method of claim 7, wherein the first notification and the second notification are at least one of audible in a cockpit of an aircraft and visible in the cockpit of the aircraft.

9. The method of claim 7, further comprising:
recording the measured concentration of the ambient aerosols in memory as a function of time if the composition information indicates the presence of volcanic ash in the air stream;
generating expected concentration of the ambient aerosols in memory as a function of time;
comparing the measured concentration of ambient aerosols as a function of time with a corresponding respective expected concentration of ambient aerosols as a function of time; and
generating a perceptible alarm in response to the measured concentration as a function of time matching within a specified threshold the corresponding respective expected concentration as a function of time.

10. The method of claim 7, further comprising:
determining an amount of volcanic ash accumulated in at least a portion of an aircraft; and
generating a perceptible alarm in response to the accumulated volcanic ash exceeding a specified threshold.

11. A system, comprising:
a memory having encoded thereon computer-executable instructions; and
a processor functionally coupled to the memory and configured, by the computer-executable instructions, to perform at least the following actions,
measuring a concentration and a size of ambient aerosols in an air stream,
providing a first notification if at least one of the size of the ambient aerosols exceeds a first threshold and the concentration of the ambient aerosols exceeds a second threshold,
determining composition information of the ambient aerosols;
providing a second notification if the composition information indicates presence of volcanic ash in the air stream,
storing electronic data representing the measured concentration of the ambient aerosols in memory as a function of time if the composition information indicates the presence of volcanic ash in the air stream,
generating expected concentration of the ambient aerosols in memory as a function of time,
comparing the measured concentration of ambient aerosols as a function of time with a corresponding respective expected concentration of ambient aerosols as a function of time, and
generating a perceptible alarm in response to the measured concentration as a function of time matching within a specified threshold the corresponding respective expected concentration as a function of time.

12. The system of claim 11, wherein determining the composition information of the ambient aerosols occurs if at least one of the size of the ambient aerosols exceeds the first threshold and the concentration of the ambient aerosols exceeds the second threshold.

13. The system of claim 11, wherein the processor is further configured for:
storing electronic data representing the size of the ambient aerosols;
processing the electronic data representing the measured concentration of the ambient aerosols and the electronic data representing the size of the ambient aerosols; and
triggering an instrument configured to determine the composition information if at least one of a portion of the electronic data representing the measured concentration exceeds the first threshold and a portion of the electronic data representing the size of the ambient aerosol exceeds the second threshold.

14. The system of claim 13, wherein the processor is further configured for:
recording electronic data representing the composition information of the ambient aerosols; and
processing the electronic data representing the composition information of the ambient aerosol,
wherein providing the first notification comprises generating an electronic signal that triggers a perceptible caution alarm if at least one of the portion of the electronic data representing the measured concentration exceeds the first threshold and the portion of the electronic data representing the size of the ambient aerosol exceeds the second threshold, and wherein providing the second notification comprises generating an electronic signal that triggers a perceptible volcanic ash warning alarm if the electronic data representing the composition of the ambient aerosol matches signature data for volcanic ash within a specified confidence level.

15. The system of claim 11, wherein the first notification and the second notification are at least one of audible in a cockpit of an aircraft and visible in the cockpit of the aircraft.

16. The system of claim 11, wherein the processor is further configured for:

determining an amount of volcanic ash accumulated in at least a portion of an aircraft; and generating a perceptible alarm in response to the accumulated volcanic ash exceeding a specified threshold.

17. A system, comprising:

a memory having encoded thereon computer-executable instructions; and a processor functionally coupled to the memory and configured, by the computer-executable instructions, to perform at least the following actions, measuring a concentration and a size of ambient aerosols in an air stream, recording electronic data representing the measured concentration and size of the ambient aerosols, processing the electronic data representing the measured concentration and size of the ambient aerosols, providing a first notification if at least one of the size of the ambient aerosols exceeds a first threshold and the concentration of the ambient aerosols exceeds a second threshold, wherein providing the first notification comprises generating an electronic signal that triggers a perceptible caution alarm if at least one of the portion of the electronic data representing the measured concentration exceeds the first threshold and the portion of the electronic data representing the size of the ambient aerosol exceeds the second threshold, triggering an instrument configured to determine composition information if the at least one of the portion of the electronic data representing the measured concentration exceeds the first threshold and the portion of the electronic data representing the size of the ambient aerosol exceeds the second threshold, determining the composition information of the ambient aerosols, recording electronic data representing the composition information of the ambient aerosols, processing the electronic data representing the composition information of the ambient aerosol, and providing a second notification if the composition information indicates presence of volcanic ash in the air stream, wherein providing the second notification comprises generating an electronic signal that triggers a perceptible volcanic ash warning alarm if the electronic data representing the composition of the ambient aerosol matches signature data for volcanic ash within a specified confidence level.

18. The system of claim 17, wherein the first notification and the second notification are at least one of audible in a cockpit of an aircraft and visible in the cockpit of the aircraft.

19. The system of claim 17, wherein the processor is further configured for:

storing the measured concentration of the ambient aerosols in memory as a function of time if the composition information indicates the presence of volcanic ash in the air stream;

generating expected concentration of the ambient aerosols in memory as a function of time;

comparing the measured concentration of ambient aerosols as a function of time with a corresponding respective expected concentration of ambient aerosols as a function of time; and generating a perceptible alarm in response to the measured concentration as a function of time matching within a specified threshold the corresponding respective expected concentration as a function of time.

20. The system of claim 17, wherein the processor is further configured for:

determining an amount of volcanic ash accumulated in at least a portion of an aircraft; and generating a perceptible alarm in response to the accumulated volcanic ash exceeding a specified threshold.

* * * * *